United States Patent
Lisec et al.

(10) Patent No.: US 7,413,710 B2
(45) Date of Patent: Aug. 19, 2008

(54) PIPETTE SYSTEM AND PIPETTE ARRAY

(75) Inventors: Thomas Lisec, Itzehoe (DE); Sascha Mühlmann, Oldendorf (DE); Sven Grünzig, Itzehoe (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 682 days.

(21) Appl. No.: 10/399,521

(22) PCT Filed: Oct. 23, 2001

(86) PCT No.: PCT/DE01/04023

§ 371 (c)(1),
(2), (4) Date: Sep. 17, 2003

(87) PCT Pub. No.: WO02/35187

PCT Pub. Date: May 2, 2002

(65) Prior Publication Data

US 2004/0050861 A1   Mar. 18, 2004

(30) Foreign Application Priority Data

Oct. 24, 2000   (DE) ................................. 100 52 819

(51) Int. Cl.
*B01L 3/02* (2006.01)
(52) U.S. Cl. .................... 422/100; 422/101; 436/180; 73/427
(58) Field of Classification Search ................. 436/180; 422/100–101; 73/427, 864.18
See application file for complete search history.

(56) References Cited

U.S. PATENT DOCUMENTS

| 4,517,302 | A | * | 5/1985 | Saros ........................ 436/180 |
| 5,183,765 | A | | 2/1993 | Qureshi et al. |
| 5,362,648 | A | * | 11/1994 | Koreyasu et al. ............. 436/48 |
| 5,550,059 | A | * | 8/1996 | Boger et al. .................. 436/54 |
| 5,639,426 | A | * | 6/1997 | Kerr et al. ................... 422/100 |
| 5,724,142 | A | | 3/1998 | Kaminski et al. |
| 5,927,547 | A | | 7/1999 | Papen et al. |
| 6,101,946 | A | | 8/2000 | Martinsky |

(Continued)

FOREIGN PATENT DOCUMENTS

CH   682847 A5   11/1993

(Continued)

OTHER PUBLICATIONS

Patent Abstracts of Japan: Kawanabe Junichi et al, "Aerial Discharge Type Dispensing Device", Publication No. 10096735 A published Apr. 14, 1998 (Application No. 08253419 filed Sep. 25, 1996).

(Continued)

*Primary Examiner*—Brian R. Gordon
(74) *Attorney, Agent, or Firm*—Breiner & Breiner, LLC (57) ABSTRACT

A pipette system including a pipette capillary tube and an actuator, with the actuator serving to set the position of a phase boundary between a system medium and a second medium in the pipette capillary is described. A sensor element is also provided for measuring the position of the phase boundary, in such a way that the actuator is controlled by a regulating element in response to an output signal from the sensor element.

27 Claims, 5 Drawing Sheets

U.S. PATENT DOCUMENTS

| | | | |
|---|---|---|---|
| 6,232,129 B1 * | 5/2001 | Wiktor | 436/180 |
| 6,296,811 B1 * | 10/2001 | Sasaki | 422/100 |
| 6,413,475 B2 * | 7/2002 | Ishizawa et al. | 422/106 |
| 6,551,558 B1 * | 4/2003 | Mann et al. | 422/100 |
| 6,669,909 B2 * | 12/2003 | Shvets et al. | 422/100 |
| 6,908,226 B2 * | 6/2005 | Siddiqui et al. | 374/45 |
| 2001/0055814 A1 * | 12/2001 | Sasaki | 436/180 |

FOREIGN PATENT DOCUMENTS

| | | |
|---|---|---|
| DE | 39 27 718 C1 | 3/1990 |
| DE | 42 14 430 A1 | 11/1992 |
| EP | 0 527 059 A1 | 2/1993 |
| EP | 0 753 721 A2 | 1/1997 |
| EP | 1 048 953 A2 | 11/2000 |
| WO | WO 96/24040 A2 | 8/1996 |
| WO | WO 99/10099 A1 | 3/1999 |
| WO | WO 00/02055 A1 | 1/2000 |
| WO | WO 01/20271 A1 | 3/2001 |

OTHER PUBLICATIONS

Patent Abstracts of Japan: Koichi Wakatake, "Pipet For Confirming Liquid Amount And Liquid Amount Confirming Method And Apparatus Using Said Pipet", JP 62-163968 (A), Jul. 20, 1987 (Application No. 61-5021 filed Jan. 16, 1986), Nitsuteku K.K.

Patent Abstracts of Japan: Koichi Wakatake, "Method And Device For Measuring Liquid By Automatic Analyzer", JP 62-168055 (A), Jul. 24, 1997 (Application No. 61-8009 filed Jan. 20, 1986), Nitsuteku K.K.

Patent Abstracts of Japan: Yasuko Takiguchi, "Suction Discharge Method For Automatic Chemical Analyzer", JP 62-228952 (A), Oct. 7, 1987 (Application No. 61-70794 filed Mar. 31, 1986), Toshiba Corp.

M. Doering, "Fluessigkeiten Mikrofein Dosieren", Feinwerktechnik + Messtechnik, Carl Hanser, Verlag., Munchen, Germany, vol. 99, No. 11, Nov. 1, 1991, pp. 459-463, XP000274115.

* cited by examiner

PIPETTE SYSTEM AND PIPETTE ARRAY

FIELD OF INVENTION

The present invention relates to a pipette system and to pipette arrays of pipette systems, comprising a control loop consisting of an actuator, a regulating element and a sensor element for controlling the pipetting operation.

The inventive pipette systems and pipette array is suitable for pipetting liquids in HTS (high throughput screening), in clinical chemistry and in chemical synthesis with particular advantages.

There are many applications, e.g. in clinical chemistry, where different volumes must be pipetted in parallel with a high precision (3% coefficient of variation in typical cases). At the same time, it is necessary to keep the minimum sample volumes as small as possible in order to minimise the consumption of reagents or in order to allow for an increasing packing density of the micro titre plates. To this end, it should be possible to transfer volumes in the sub-micro litre range by means of an array of actively controlled, individually controllable pipettes.

BACKGROUND OF THE INVENTION

The use of syringe pumps as driving means for pipetting slight quantities of liquids is common. As advanced syringe pumps are based on stepping motors with a high resolution the high-precision manipulation of liquid quantities in the nano litre range is possible. Common needle-type pipetting devices comprise a single channel consisting of a syringe pump fixedly mounted in the housing, which is connected via a hose filled with the liquid to the three-dimensionally displaceable pipetting needle. As the connecting hose may be deformed when the needle is displaced and as its volume does hence not remain constant the minimum pipetting volume is limited to the micro litre range. Such devices are used, for instance, for hit picking in HTS applications where samples from isolated wells of a major number of micro titre plates are combined on a new micro titre plate. As each micro titre plate must be serially processed needle-type pipetting devices are often equipped with several pipetting channels. When each channel must be separately controlled a corresponding high number of syringe pumps are required. Large-size systems of this kind are provided with 96 channels, for instance, whereof respective groups of 8 are operated in parallel by means of one syringe pump. The installation of 96 syringe pumps is not possible for reasons of space and costs.

Equipment in which an array of pipettes is operated on the plunger stroke principle constitutes one alternative of the needle-type pipetting devices. In configurations with a single plunger, the samples are manipulated via an air cushion. In view of the size of the air cushion between the plunger and the samples, the minimum volume that can be pipetted with a high precision is limited to the micro litre range. Other configurations consist of an array composed of individual syringes.

As only small air cushions are created in each syringe the transfer of distinctly smaller quantities is possible. For example, a minimum pipetting volume of 100 nano litres is quoted for these devices. All the devices of this type share the common aspect that the pipettes cannot be controlled individually but operate always in parallel. Their principle field of application is therefore the HTS domain where as many samples as possible must be transferred and measured at a constant volume with a maximum rate from one micro titre plate to another plate. The pipetting precision remains comparatively low, which restricts the application to tests of a predominantly qualitative nature.

SUMMARY OF THE INVENTION

The present invention is based on the problem of providing a pipette system that avoids the disadvantages in prior art and allows particularly for the precise control of each individual pipette within a pipette array consisting of inventive pipette systems.

The present invention provides a method of operating the pipette system and/or pipette arrays composed thereof.

The preferred embodiments are the subject matters of the dependent claims.

The inventive pipette system comprises a pipette capillary tube, an actuator, a regulating element and a sensor element. In combination with the regulating element and the actuator, the sensor element constitutes a control loop for controlling the pipetting operation. The pipette capillary tube is filled with a system medium at least partly. The actuator allows for the shift of the position in space of a phase boundary between the system medium and a second medium inside the capillary tube. The term "phase boundary" is to be understood here as denoting any sufficiently distinct transition between different media. Hence also the transition between a liquid and a gas, for example.

The phase boundary is preferably the boundary of a bubble of the second medium within the system medium. The sensor element is so designed that it is able to detect the position of the phase boundary or the bubble inside the capillary tube. The sensor element cooperates with the regulating element and the actuator to form a control loop in such a way that the shift of the position of the system medium within the pipette capillary tube by means of the actuator can be controlled via the regulating element as a function of the position of the phase boundary or the bubble, which is measured by means of the sensor element. The sensor element is hence connected by an electronic circuit to the actuator, which circuit detects and processes the output signals from the sensor element and is capable of selectively controlling the actuator in response to thee signals. The actuator may either cause by itself the system medium to move, i.e. create a flow, or it may be configured, e.g. in the form of a valve, in such a way that it can control and/or influence a flow of the system medium, which can be created by means of an outside driving means. The phase boundary can hence be selectively positioned within the capillary tube by suitable control of the actuator with simultaneous activation of the driving means within a monitored region. The driving means consists preferably of a reservoir containing the system medium, which is so connected to the pipette capillary tube that some system medium may flow out of the reservoir and into the pipette capillary tube. For instance, the reservoir may be connected via a hose to one end of the pipette capillary tube. The system medium inside the reservoir can be subjected to pressure in such a way that a driving means is created for a flow of the system medium in the pipette capillary tube. In certain cases, the actuator and the driving means may coincide. When, for instance, the equipment is provided with a single pipette only it is also possible to control a syringe pump directly by means of the output signal from the sensor element. The collection and discharge of gaseous or liquid samples via a pipetting tip is correlated with the position of the monitored phase boundary within the capillary tube. The collected or discharged sample volume is here proportional to the change in the position of the phase boundary.

On principle, any liquid or any gas whatsoever comes into question as system medium; preferably, an electrically conductive liquid is employed. When the system medium is a liquid the second medium may be either a gas or another liquid immiscible with the system medium. When both media are liquids there must be a significant difference in conductivity between the liquids when a conductivity sensor is employed. Without any restriction of the general applicability, mostly liquids will be mentioned in the following. These liquids are also referred to as system liquid. Any aqueous or non-aqueous liquid whatsoever may be used as system liquid, which is compatible with the materials used in the pipette.

A sensor according to the German patent application DE 199 44331 is used as sensor element. This sensor is a micro sensor for measuring the position of liquids in capillary tubes and is based on the principle of conductivity measurements. However, only a change in the conductivity is essential for the measuring principle. The absolute amount of conductivity of the operating liquid is of minor importance only. Whenever such a sensor is employed the system liquid must be electrically conductive unless the second medium is electrically conductive. The capillary contains a gas bubble enclosed on both sides by the operating solution; this bubble can be moved to and from inside the capillary over a sensor chip. It is also possible to use a non-conductive liquid instead of the gas bubble, which is immiscible with the operating solution. Without any restriction of the general applicability, only a bubble will be mentioned in the following. What is essential is the fact that there is a significant difference in conductivity between the operating liquid and the contents of the bubble. It is therefore equally conceivable that the operating liquid is not conductive whilst the bubble consists of a conductive liquid. Hence, there is at least one boundary between two different conductivities in the charge contained in the capillary tube in the area above the sensor element. The sensor chip consists of a substrate, preferably made of silicon, glass or synthetic resin. Micro-structured, partly passivated metal electrodes, preferably made of platinum, iridium or gold, are applied on the chip. Iridium excels itself by a particularly low polarisation resistance in an aqueous solution. The electrodes consist of a respective, preferably constant, number of sub-electrodes spaced from each other, preferably at constant distances, which are interlinked to each other by means of electrical connections. The sub-electrodes of preferably two electrodes are opposite to each other in pairs, preferably at a constant spacing, in the form of pairs of sub-electrodes. The repetitive basic geometry (meanders) hence consists of preferably two pairs of electrodes that consist, in their turn, of pairs of sub-electrodes. This fundamental geometry is periodically repeated over the entire length of the sensor chip. The distance between the pairs of sub-electrodes in the longitudinal direction, i.e. in the direction of the bubble movement to be measured, is preferably permanently the same. This applies also to adjacent pairs of sub-electrodes appertaining to neighbouring meanders. The electrical connections between the sub-electrodes of the electrodes are preferably coated with a passivating layer whereas the sub-electrodes as such constitute the sensor-active regions of the sensor chip and are therefore located directly on the surface coming into contact with the operating liquid. The electrical connections may be positioned in such a way that the wall of the capillary tube seals them completely from the inner space in the capillary tube. When the capillary tube is made of an insulating material a passivating layer may be omitted. Passivation is required only when the electrical connections may come into contact with the system liquid or when the capillary tube consists of an electrically conducting material. The sensor is mounted laterally on the capillary tube, which consists of glass or synthetic resin, for instance, in such a way that the active regions of the electrodes, i.e. the sub-electrodes, are located in the interior space of the capillary tube. The terminals (bond pads) of the electrodes of the individual meanders, by contrast, are located outside the capillary tube. To this end, the wall of the capillary tube is partially replaced by the sensor chip. When a conductive liquid is contained in the capillary tube and when a voltage is applied current flows between the opposite sub-electrodes of a meander. The impedance of the meander is determined, inter alia, by the wetted electrode surface, i.e. the number of the wetted pairs of sub-electrodes. As the wetted area is enlarged the impedance is reduced. This effect may be utilised for detecting the position of an air bubble or generally a conductivity boundary, which covers the meander completely or partly or which is located, in the case of an isolated conductivity boundary, above the meander. For the description of the mode of operation of the sensor only a bubble will be mentioned in the following, without any restriction of the general applicability. The statements are valid, however, also for the presence of a single conductivity boundary. In such a case the position of the conductivity boundary between two pairs of sub-electrodes of a meander or the position of the conductivity boundary between two meanders is determined rather than the position of a bubble. A bubble is a special case in which two conductivity boundaries are located within the charge contained in a capillary tube.

In the quiescent state, the position of the bubble can be determined on the basis of the comparison of the resistance values of all meanders. All the meanders wetted by the liquid present a slight resistance, independently of the concrete operating liquid. When the bubble has a sufficient size so that at least one meander is completely covered by it a maximum resistance value is achieved for this meander. The adjoining, only partly covered meanders present intermediate values for the resistance. The determination of the precise position of the liquid surface in the intermediate zone of a meander requires that the shape of the resistance curve (reference resistance graph) in scanning of a meander and the maximum and minimum value of the resistance of the respective meander are known. With an interpolation on the graph of known shape and with the minimum or maximum value being known, it is possible to assign each intermediate resistance value to a particular pair of sub-electrodes of the respective meander—and hence the position of the bubble or the position of the conductivity boundary—can be precisely determined. When the wetting properties of the operating liquid relative to the sensor element are of such a nature that a permanent liquid film is not formed on the sensor element and when the rate of migration of the bubble is not excessively high characteristic abrupt changes in the resistance (jumps) occur during the movement of the bubble over the pairs of sub-electrodes in a meander. In the event of an aqueous solution this means a hydrophobic surface of the sensor element, however on the condition that the solution must not be repelled so strongly that wetting cannot be created in those areas of the sensor element which are covered by the operating liquid. In an ideal case, the sensor element is always wetted by the operating liquid exactly at those sites where it is covered by the level of the operating liquid. When all meanders are monitored in parallel the distance covered by the bubble and hence the moved liquid volume can be determined from the total number of jumps during the migration of the bubble.

In a pipette array constituted by pipettes with inventive pipette systems, all the pipettes can be controlled separately.

In correspondence with the activation of the drive means (negative pressure or overpressure) it is possible to collect and also discharge different sample volumes independently of each other. It may, however, also be expedient to control the pipettes only in one sense, i.e. either when samples are collected or when samples are discharged, and to cause the pipettes to operate in parallel in the respectively other sense.

As the charging level in the pipette is monitored by means of the sensor it is not necessary that the actuator operation is as precise as the operation of a syringe pump, for example; the actuator may rather be controlled in response to the sensor signal. At the same time, different actuators and drive means can be combined with each other.

As the actuator and the sensor element may be installed in the pipette capillary tube directly and as the regulating element requires only little space the inventive pipette systems enables the design of pipette arrays whose individual pipettes can be controlled independently of each other and are each capable of pipetting sample volumes of different quantities.

BRIEF DESCRIPTION OF THE DRAWINGS

The present invention will be described by embodiments in the following, without any restriction of the general inventive idea, with reference being made to the drawing.

DETAILED DESCRIPTION OF THE INVENTION

Figure 1:
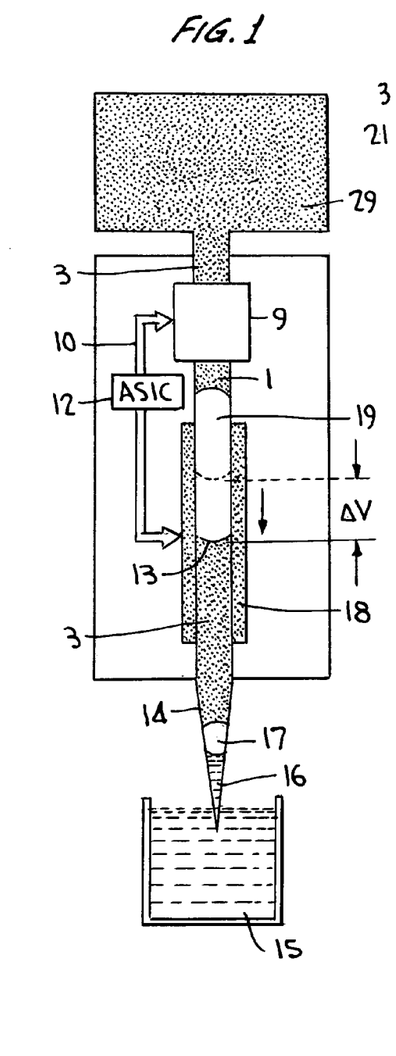
FIG. 1 illustrates an inventive pipette system.

FIG. 1 is a schematic view of the structure of a controllable pipette with the inventive pipette system. The pipette is provided with a filling level sensor (18) inside a capillary tube (1). The filling level sensor consists of a chip mounted laterally along the longitudinal direction, which is capable of continuously monitoring the position of a phase boundary (13) inside the capillary tube, preferably between air and a liquid. In the case where the filling level sensor is designed as sensor element in correspondence with the German Patent Application DE 199 44 331, the chip contains micro-structured metal electrodes whose active zones are located inside the capillary tube. They are distributed over the entire length of the chip, with a certain arrangement—that will also be referred to as "meander" in the following—being continuously repeated. An actuator (9), which is capable of taking an active influence on a current flowing through the capillary tube, is provided on the upper end of the capillary tube of the filling level sensor. The current may be a liquid flow or a gas flow. In the following a liquid flow will be referred to, without limiting the general applicability. The actuator may be an electromagnetic valve, for instance. A regulating element (12) consisting of an electronic circuit such as an ASIC circuit, for example, connects the filling level sensor and the actuator in a control loop (10). All the components forming part of the pipette system are enclosed by the dotted frame in the figure.

The upper output of the pipette is connected to a drive means (29) that is capable of creating a fluid flow, i.e. movement of a liquid in the pipette, by acting via pneumatic or hydraulic force. The system liquid (3) in the pipette encloses a bubble of a second medium (19), e.g. an air segment—referred to a measuring bubble in the following—whose first phase boundary—also referred to as meniscus in the following—is located within the active electrode zones of the filling level sensor inside the capillary tube. A preferably exchangeable pipette tip (14) is connected to the lower output of the pipette. A sample (16) may be present in the tip. The sample can be aspirated from a sampling receptacle (15) into the pipetting tip or may be discharge therefrom when the drive means creates a negative pressure or overpressure via the actuator on the system liquid. The sample solution is separated from the system liquid by a further air segment, referred to as "separating bubble (17)" in the following.

When the measuring bubble and hence the monitored phase boundary is shifted inside the capillary tube the position of the phase boundary or the measuring bubble is detected by the filling level sensor in compliance with the static method of filling level detection described in the following, if the sensor according to the German Patent Application DE 199 44 331 is employed. Each meander of a sensor, which is completely covered by the system liquid, presents a maximum value of the output signal. When, by contrast, any meander whatsoever is completely covered by the air bubble its output signal is zero. When any meander whatsoever is covered by the air bubble only partly, i.e. when the phase boundary between the system liquid and the air is located within this particular meander, intermediate values are detected. When the maximum values are known for all meanders the intermediate values of each meander can be assigned to one of the electrode pairs of the respective meander by interpolation on a line between zero and the maximum value, and thus the position of the phase transition can be unambiguously determined over the entire length of the sensor. And vice versa, when the maximum value is known it is possible to calculate concrete values of the output signal for each meander of a sensor, which values would correspond to a specific position of the monitored phase boundary. The prerequisite for this method is the fact that the maximum values of all meanders of the sensor do not change during the dosing operation.

When the cross-section of the capillary tube remains constant over its length the shift of the monitored phase boundary is proportional to the volume of system liquid, which is displaced out of the capillary tube in an upward or downward direction. When the monitored phase boundary migrates downward, for instance, the displaced system liquid in its turn presses one part of the sample out of the pipette tip. When the separating bubble is sufficiently small so that the compressibility of air can be neglected the discharged sample volume corresponds to the volume of the displaced system liquid with a high accuracy. When the monitored phase boundary is shifted upwards and the pipette tip is immersed into a sampling receptacle a sample volume is collected that is equivalent to the shift.

As the actuator is connected to the sensor via an electronic control system (ASIC) the phase transition can be precisely positioned by a suitable control of the actuator with a simultaneous activation of the drive means (overpressure or negative pressure) within the region of the capillary tube, which is monitored by the filling level sensor. In this manner, it is hence possible to collect or discharge precisely defined sample volumes.

Figure 2:
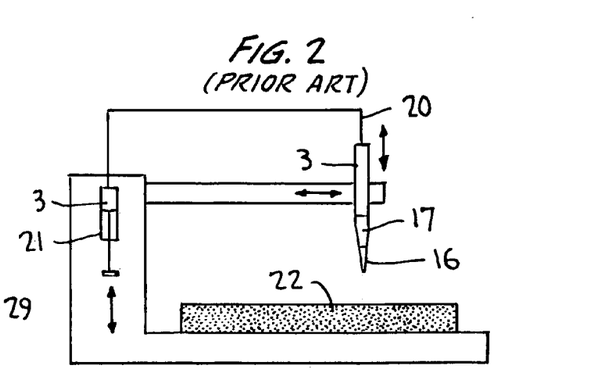
FIG. 2 shows the structure of a pipette system according to prior art.

FIG. 2 shows a prior art needle-type pipetting device with a single channel, consisting of a syringe pump (21) fixedly mounted n the housing, which is connected via a hose (20) filled with a liquid to the pipetting needle mobile in three dimensions. The pipette is operated by a syringe pump by means of a system liquid (3) and can be displaced over the micro titre plate (22). The air bubble (17) in the pipette tip (14) serves to separate the system liquid from the sample (16).

Figure 3A:
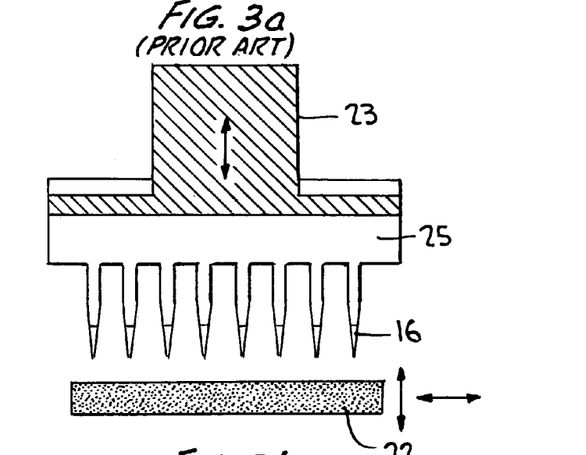
FIG. 3 is a view of the structure of prior art pipette arrays operating on the plunger stroke principle, with pipettes operating in parallel.
Figure 3B:
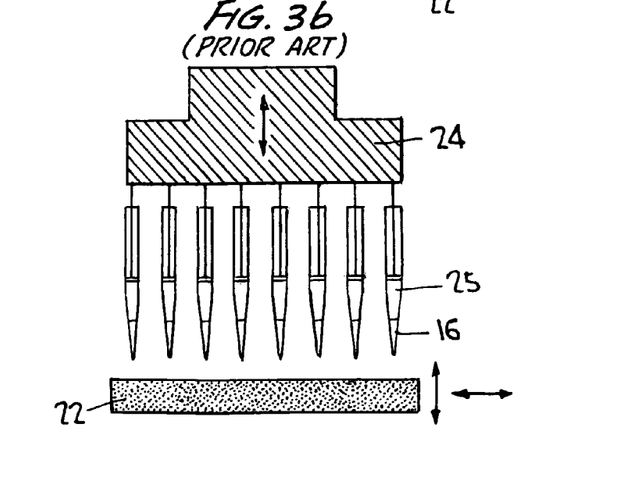

FIG. 3 is a schematic view of conceivable variants of prior art equipment in which an array of pipettes operating in parallel is operated on the plunger stroke principle. In the design according to FIG. 3a, the samples (16) are manipulated via an air cushion (25) by means of a single plunger (23). Due to the size of the air cushion between the plunger and the samples, the minimum volume that can be precisely pipetted, is limited to roughly 1 micro litre. The design according to FIG. 3b corresponds to an array of individual syringes that are operated by means of a plunger array (24). As only small or no air cushions (25) at all are created in each syringe it is possible to transfer distinctly smaller sample quantities (16).

Figure 4:
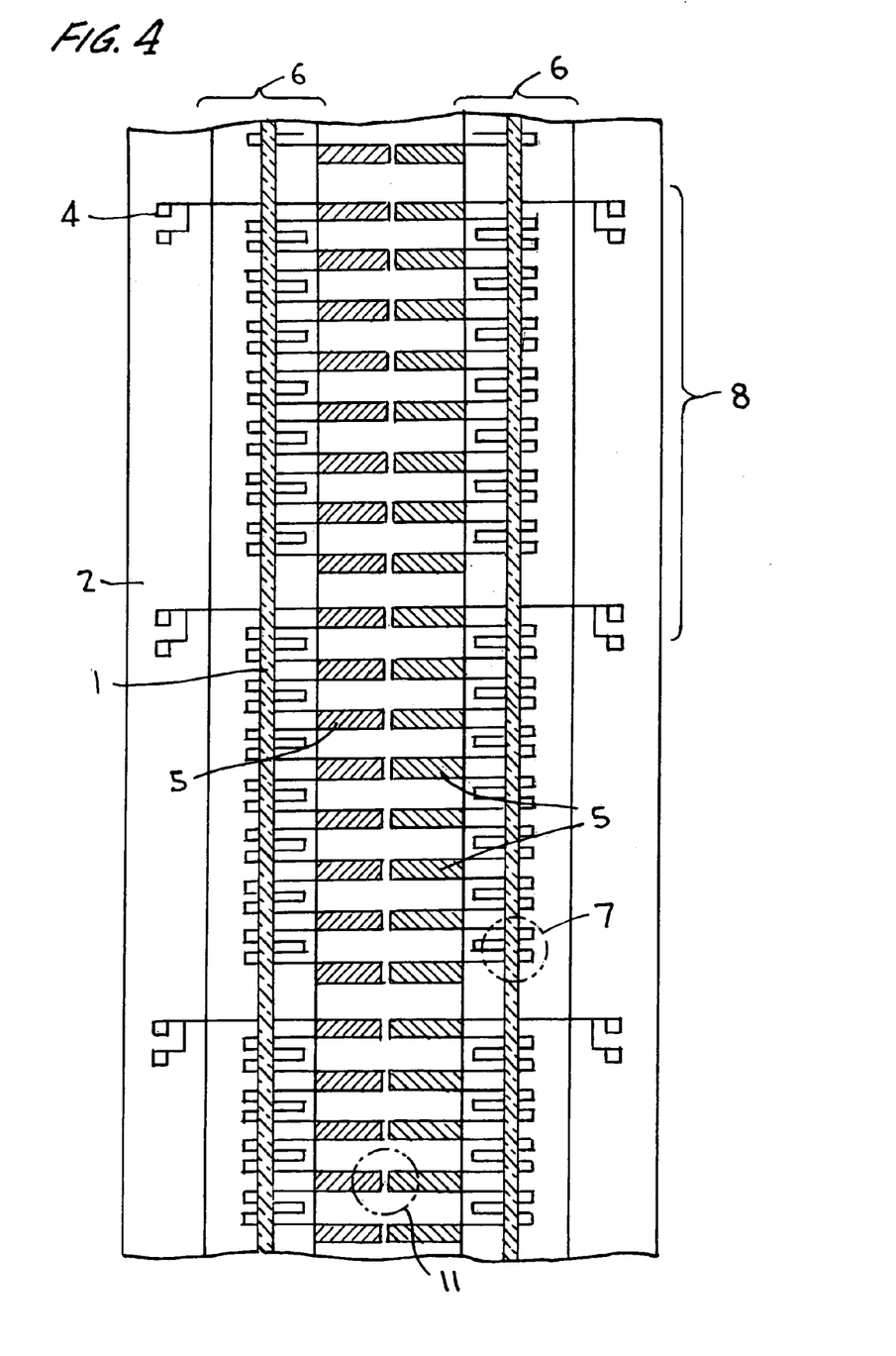
FIG. 4 illustrates an electronic sensor according to the German patent application DE 199 44 331.

FIG. 4 shows a detail of a sensor according to the German Patent Application DE 199 44 331 with a preferred electrode geometry in a plan view. The active exposed regions (5) of the electrodes are located within a capillary tube (1) and are distributed over the entire length of the sensor chip (2). The electrode structure consists here of a continuously repeated arrangement. Each electrode consists of several sensor-active sub-electrodes (5), with two electrodes always constituting a pair of electrodes (meander) (8). The sub-electrodes of the pairs of electrodes are opposing each other as pairs of sub-electrodes (11). Each electrode presents a separate potential electrical terminal (bond pad) (4). Successive meanders are so arranged that the distance between pairs of sub-electrodes (11) is permanently constant over the entire length of the chip. Each meander consists of two metal electrodes with 8 mutually opposing pairs of sub-electrodes. The individual sub-electrodes on each side of a meander are connected in series. The electrical connection between the individual sub-electrodes on one side of a meander presents an ohmic resistance that should not be too small. In the illustrated embodiment, the resistance is increased when the electrical connection (7) is prolonged in the form of wavy lines. The distance between neighbouring pairs of sub-electrodes (11) in the longitudinal direction is always the same. A spacing of the sub-electrodes in the longitudinal direction by a few 10 micro metres is preferred. The smaller the spacing of the pairs of sub-electrodes is in the longitudinal direction, the higher is the resolution of the sensor, i.e. the smaller are the liquid quantities that can be dosed. The exposed active electrode regions may come into contact with a liquid inside the capillary tube. The outlets to the bond pads provided outside the capillary tube are covered by a passivating layer (6) unless they are covered by the wall of the capillary tube.

Figure 5:
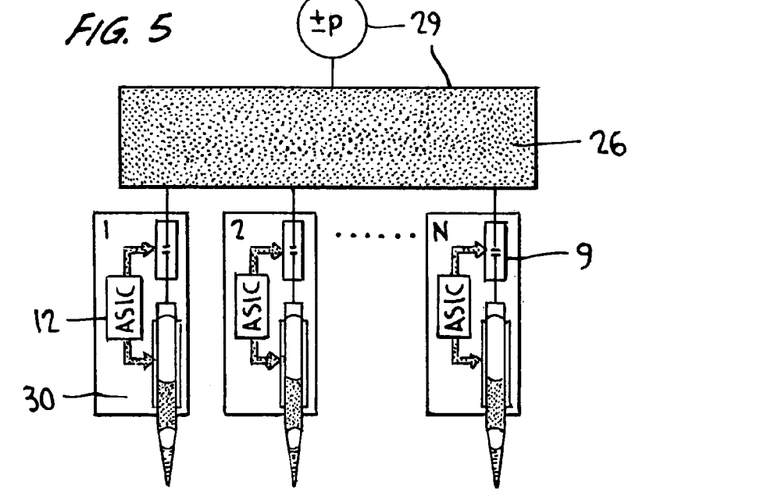
FIG. 5 shows an inventive pipette arrays with valves as actuators.

The structure illustrated in FIG. 5 shows a dosing equipment including an array of N individually controllable and adjustable pipettes (30) that are provided with electromagnetic valves as actuators (9). Miniature valves corresponding to the structural module of a 96-element micro titre plate are commercially available. The valve is controlled via a circuit (ASIC) integrated as regulating element on the pipette for processing the sensor signals. The drive means (29) is constituted by a common reservoir (26) at the upper outlet of the pipettes, in which a pneumatically or hydraulically defined negative pressure or overpressure (±p) can be generated, for example. In the present embodiment, only one common drive means is used for all pipette systems.

Figure 6:
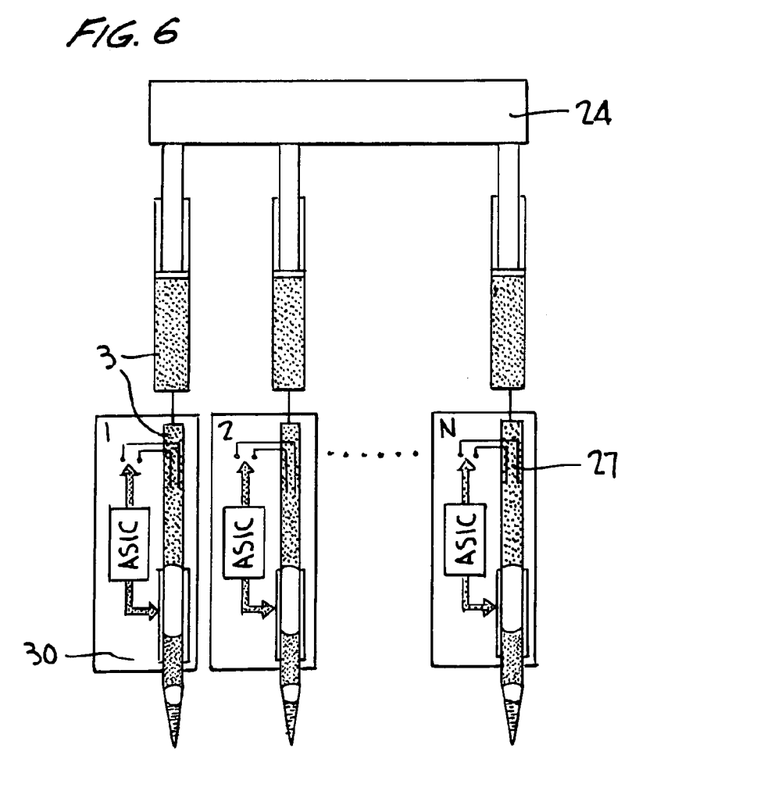
FIG. 6 is a view of an inventive pipette array with electrolytic cells as actuators and a plunger arrays as external drive means.

FIG. 6 illustrates another variant of the device with N individually controllable and adjustable pipettes (30). In this case, each pipette includes an electrolytic cell (27) as actuator. When the system liquid (3) is an aqueous solution the application of an electric voltage causes the production of gas in the electrolytic cell and consequently the establishment of a pressure in the pipette. When the volume above each pipette is invariable so that the system liquid cannot escape in an upward direction some sample liquid is displaced out of the pipette tip in correlation with the gas volume so created. This process can be controlled in compliance with predetermined nominal values, in analogy to the valve, via the ASIC element integrated into the pipette. Here a plunger array (24) or even a syringe pump may be used as drive means, for instance. The gas bubbles could also be created by heating the system liquid above the sensor element. Another variant of the actuator could be realised by narrowing or widening the diameter of the capillary tube above the sensor element. To this end, it is possible, for instance, to exert a pressure from the outside via a conventional sensor element or a bimetal strip on a deformable hose section joining the pipette capillary tube above the sensor element, under control of the output signal from the sensor element.

FIG. 7 uses the equipment shown in FIG. 5 to illustrate the operation of the parallel transfer of samples (16) of different volumes from a micro titre plate (22) to another plate. Each of the flow directions are indicated by respective arrows in the figures.

First of all, all the pipettes are flushed with the system liquid (3). To this end, a defined overpressure "+p" must be set in the reservoir (26), then all the actuator valves (9) "one" to N must be opened simultaneously and closed again after a predetermined interval. In accordance with FIG. 7a, then all pipettes are completely charged with the system liquid. When a sensor according to the German Patent Application DE 199 44 331 is employed, now the maximum output signals of meanders can preferably determined and stored as reference values for each sensor.

Figure 7A:
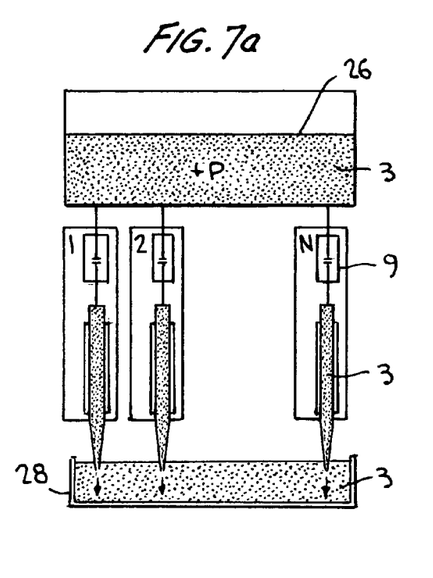
FIG. 7 shows the operation of charging an inventive pipette array with the system medium, with the subsequent pipetting operation.
Figure 7B:
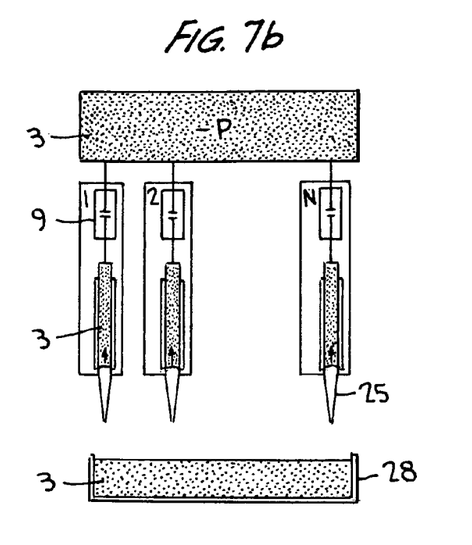

In the second step shown in FIG. 7b, a measuring bubble is created in each pipette. To this end, the reservoir is switched over to negative pressure "−p" and all valves are opened at the same time, with the pipette tips being raised above the level of the system liquid in a flushing trough (28). As a result, air (25) is aspirated into each pipette. The process is stopped by closing the valves when the upper meniscus of the air bubble in each pipette has reached a predetermined position within the sensor region. It is preferred that the same position is selected for all pipettes in order to obtain measuring bubbles of the same size. The predetermined position of the sensor region is preferably located at the lowermost meander when a sensor according to the German Patent Application DE 199 44 331 is employed.

Figure 7C:
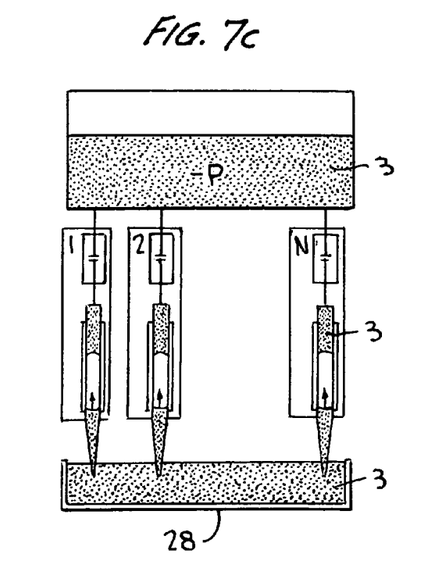

Subsequently, the pipette array is lowered into a trough containing the system liquid (flushing trough (28)) until the pipette tips are immersed into the system liquid (3), as is illustrated in FIG. 7c. When the valves are now opened simultaneously and when a negative pressure (−p) prevails in the reservoir some system liquid is aspirated. The process is stopped by closing the valve for each pipette individually when the lower meniscus in the pipette has reached the desired position that is preferably the same for all pipettes. When the sensor element according to the German Patent Application DE 199 44 331 is employed this position is preferably located on one of the lowermost meanders so that the most voluminous sample possible can be collected.

Figure 7D:
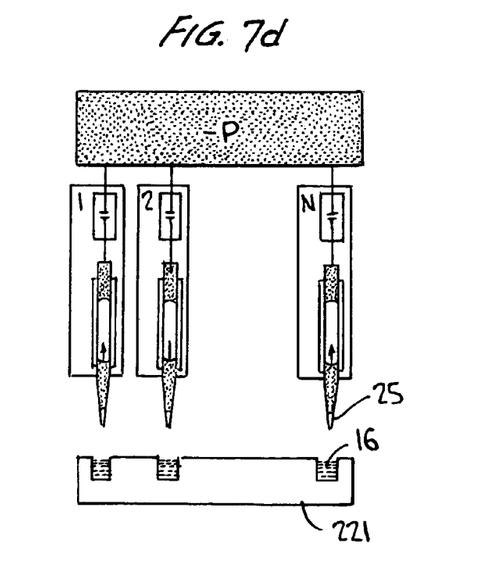

In the fourth step, the separating bubbles are created in the pipette tips, which are intended to avoid a mixture of the samples with the system liquid. To this end, the pipette array is raised until the contact of all tips with the liquid is interrupted. Like in the previous steps, the aspiration of air (25) is started by simultaneously opening the valves and monitored at the lower phase boundary of the measuring bubble, independently for each pipette. In correspondence with the nominal value, the valve of each pipette is closed individually at a certain more upward position of a certain meander. This process is illustrated in FIG. 7d. This position need not be always the same. Depending on the sample volumes or the properties of the sample solutions (16), the separating bubbles may be created in different sizes from one pipette to the next one.

Figure 7E:
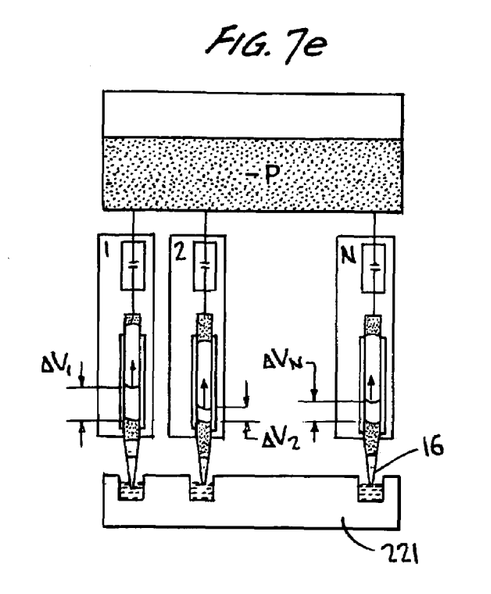

The pipette systems are now ready for pipetting sample liquids. To this end, the pipette array is positioned over a source micro titre plate (221) and lowered into the wells containing the samples (16) until the pipette tips are immersed into the liquids contained therein. Independently of the other pipettes, the valve is opened for each pipette and sample liquid is aspirated until the monitored lower phase boundary of the measuring bubble has reached the predetermined position. Then the valve is closed again. In this manner, each pipette may accommodate a different volume $\Delta V_1$ to $\Delta V_N$, as is illustrated in FIG. 7e. The starting time can here be selected individually for each pipette. For instance, all of the pipettes can be started at the same time and stopped, correspondingly, with an offset in time. They can also be started with an offset in time so that the collection of the samples (16) is completed at the same time. When all the pipettes have terminated the operated the pipette array is raised again.

Figure 7F:
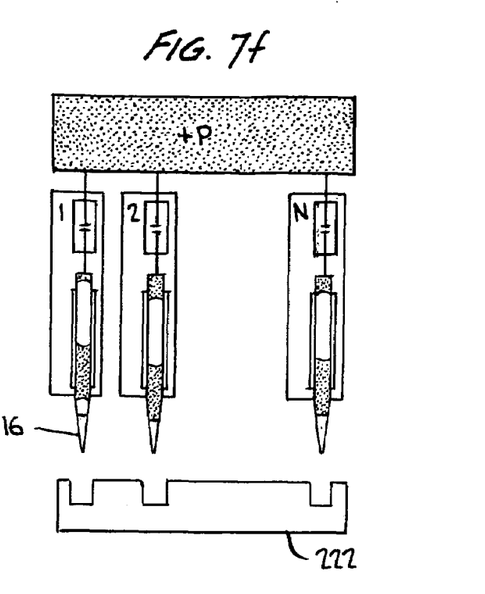
Figure 7G:
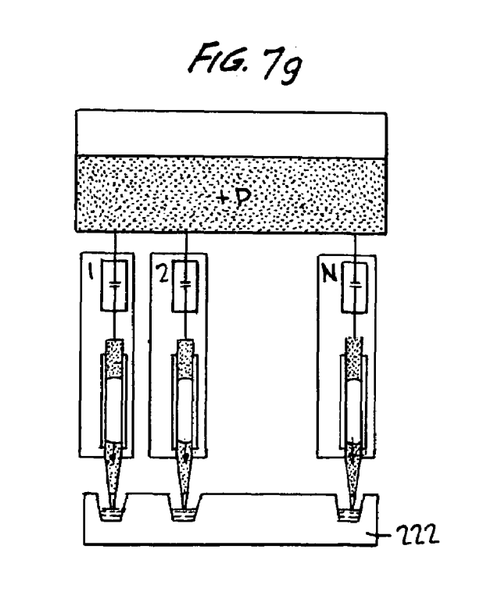
Figure 7H:
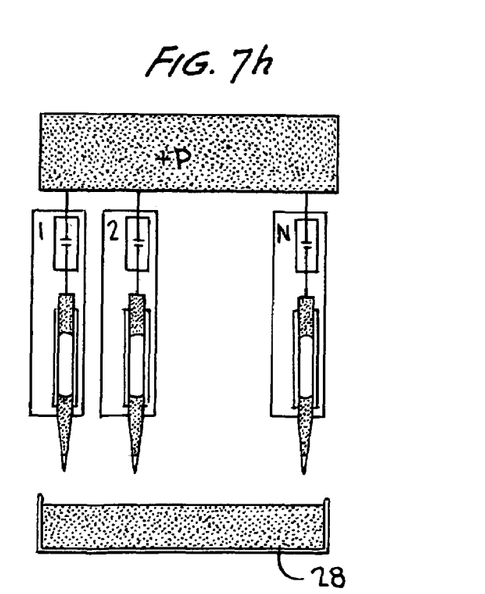

For discharge of the pipetted samples the reservoir is switched over to overpressure "+p" according to FIG. 7f, and then the pipette array is positioned above the target plate (222). After the pipettes have been lowered—cf. illustration in FIG. 7g—the valves are opened and the samples are discharged partly or almost completely, as is required in each case. As soon as the monitored phase boundary of a pipette has reached the predetermined position (nominal value) the respective valve is closed. When this procedure has been terminated for all pipettes the pipette array is raised, as is illustrated in FIG. 6h. Then further micro titre plates can be charged (cf. FIG. 7g) or a new dosing cycle may commence (cf. FIG. 7a).

In the device illustrated in FIG. 6, the steps shown in FIGS. 7b to 7d are carried out in parallel for all pipettes whilst the measuring and separating bubbles are of the same size for all pipettes. All of the collected sample volumes—cf. FIG. 7e—are equally the same. In the discharge operation according to FIG. 7g, by contrast, the pipettes can be controlled separately.

| List of reference numerals | |
|---|---|
| 1 | capillary tube, pipette capillary |
| 2 | sensor chip |
| 3 | system medium |
| 4 | potential terminals (bond pad) |
| 5 | sensor active sub-electrodes |
| 6 | passivating layer |
| 7 | connection between the sub-electrodes |
| 8 | pair of electrodes |
| 9 | actuator |
| 10 | control loop |
| 11 | pair of sub-electrodes |
| 12 | regulating element |
| 13 | phase boundary |

-continued

| List of reference numerals | |
|---|---|
| 14 | pipette tip |
| 15 | sampling receptacle |
| 16 | sample |
| 17 | separating bubble |
| 18 | sensor element |
| 19 | bubble of the second medium |
| 20 | hose |
| 21 | syringe pump |
| 22 | micro titre plate |
| 221 | source plate |
| 222 | target plate |
| 23 | plunger |
| 24 | plunger array |
| 25 | air |
| 26 | system medium reservoir |
| 27 | electrolytic cell |
| 28 | flushing trough |
| 29 | drive means |

The invention claimed is:

1. Pipette system comprising
   a pipette capillary tube,
   an actuator for setting a position of a phase boundary between a system medium and a second medium in said pipette capillary tube,
   a sensor element for measuring the position of the phase boundary, and
   a regulating element which controls said actuator in response to an output signal from said sensor element, wherein said sensor element is an electric sensor including a substrate and a plurality of electrodes applied on said substrate and adapted to be contacted individually at potential electric terminals, wherein said electrodes include sensor-active sub-electrodes linked by electrical connections to form a network, and wherein said sub-electrodes of two respective electrodes oppose each other at a spacing as pairs of sub-electrodes, with pairs of said electrodes so formed periodically repeating over a length of said sensor.

2. Pipette system according to claim 1, wherein said phase boundary is a phase boundary between a liquid as said system medium and a gas as said second medium or between an electrically conductive liquid and an electrically non-conductive liquid, wherein said conductive liquid and said non-conductive liquid are immiscible.

3. Pipette system according to claim 1, wherein said phase boundary is formed by a bubble of said second medium being enclosed between said system medium inside said pipette capillary.

4. Pipette system according to claim 2, wherein said phase boundary is formed by a bubble of said second medium being enclosed between said system medium inside said pipette capillary.

5. Pipette system according to claim 3, wherein said bubble is an air bubble and said system medium is an aqueous solution.

6. Pipette system according to claim 4, wherein said bubble is an air bubble and said system medium is an aqueous solution.

7. Pipette system according to claim 1, 2, 3, 4, 5 or 6, further comprising a drive means to create by a pneumatic or hydraulic force a flow of said system medium in said pipette capillary tube.

8. Pipette system according to claim 7, wherein said drive means is a reservoir containing said system medium, and said reservoir is connected to one end of said pipette capillary tube.

9. Pipette system according to claim 8, wherein said drive means is a plunger driver or a syringe pump driver and/or wherein said actuator controls the flow.

10. Pipette system according to claim 1, wherein said actuator is a mechanical or electro-mechanical valve or an electrolytic cell.

11. Pipette system according to claim 1, wherein said regulating element is an electronic circuit.

12. Pipette system comprising
a pipette capillary tube,
an actuator for setting a position of a phase boundary between a system medium and a second medium in said pipette capillary tube,
a sensor element for measuring the position of the phase boundary, and
a regulating element which controls said actuator in response to an output signal from said sensor element, wherein said sensor element is an electric sensor including a substrate and a plurality of electrodes applied on said substrate and adapted to be contacted individually at potential electric terminals, wherein said electrodes include sensor-active sub-electrodes linked by electrical connections to form a network, wherein said sub-electrodes of two respective electrodes oppose each other at a spacing as pairs of sub-electrodes, with pairs of said electrodes so formed periodically repeating over a length of said sensor, and wherein said sensor is fastened on said pipette capillary tube in such a way that said sensor-active sub-electrodes are located inside said pipette capillary tube, said potential electric terminals are outside said pipette capillary tube, and at least one phase boundary is present in a region of said sensor.

13. Pipette array comprising a plurality of said pipette system according to claim 1, 2, 3, 4, 5 or 6.

14. Pipette array comprising a plurality of said pipette system according to claim 10, 11 or 12.

15. Pipette array comprising a plurality of said pipette system according to claim 7.

16. Pipette array according to claim 13, wherein each of said plurality of said pipette system is individually controllable either in an operating stage "collection" or in an operating stage "discharge" of sample liquid.

17. Pipette array according to claim 14, wherein each of said plurality of said pipette system is individually controllable either in an operating stage "collection" or in an operating stage "discharge" of sample liquid.

18. Pipette array according to claim 15, wherein each of said plurality of said pipette system is individually controllable either in an operating stage "collection" or in an operating stage "discharge" of sample liquid.

19. Method of charging the pipette capillary tube of the pipette system according to claim 1 comprising:
completely charging said pipette capillary tube of said pipette system with said system medium,
creating a bubble of said second medium by aspirating said second medium and by subsequently aspirating a portion of said system medium,
aspirating a gas bubble for separating said system medium from a sample liquid to be pipetted in such a way that the phase boundary between said system medium and said second medium is located within a length of said sensor.

20. Method of charging the pipette capillary tube of said pipette array of claim 13 comprising:
completely charging said pipette capillary tube of said pipette system with said system medium,
creating a bubble of said second medium by aspirating said second medium and by subsequently aspirating a portion of said system medium,
aspirating a gas bubble for separating said system medium from a sample liquid to be pipetted in such a way that the phase boundary between said system medium and said second medium is located within a length of said sensor.

21. Method according to claim 19, wherein after the operating step of completely charging said pipette capillary tube, said method further comprises conducting reference measurements on said system medium by said sensor element.

22. Method according to claim 20, wherein after the operating step of completely charging said pipette capillary tube, said method further comprises conducting reference measurements on said system medium by said sensor element.

23. Method according to claim 19, wherein expansion of the bubble of said second medium corresponds to a length of the sensor.

24. Method according to claim 20, wherein expansion of the bubble of said second medium corresponds to a length of the sensor.

25. Method according to claim 19 or 21, wherein each said pipette system is individually controlled either in an operating stage "collection" or in an operating stage "discharge" of sample liquid.

26. Method according to claim 20, wherein each said pipette system is individually controlled either in an operating stage "collection" or in an operating stage "discharge" of sample liquid.

27. Method according to claim 22, wherein each said pipette system is individually controlled either in an operating stage "collection" or in an operating stage "discharge" of sample liquid.

* * * * *

UNITED STATES PATENT AND TRADEMARK OFFICE
CERTIFICATE OF CORRECTION

| | | |
|---|---|---|
| PATENT NO. | : 7,413,710 B2 | Page 1 of 1 |
| APPLICATION NO. | : 10/399521 | |
| DATED | : August 19, 2008 | |
| INVENTOR(S) | : Thomas Lisec et al. | |

It is certified that error appears in the above-identified patent and that said Letters Patent is hereby corrected as shown below:

<u>On the Title Page,</u>
Item (86) "§371 (c)(1), (2), (4) Date:   Sep. 17, 2003" should read
    -- §371 (c)(1), (2), (4) Date:   May 6, 2003 --.

<u>Column 2,</u>
Lines 13-14, delete the sentence "The preferred embodiments are the subject matters of the dependent claims.".

Signed and Sealed this

First Day of September, 2009

David J. Kappos
*Director of the United States Patent and Trademark Office*